United States Patent [19]

Sklenak et al.

[11] Patent Number: 5,068,086
[45] Date of Patent: Nov. 26, 1991

[54] METHOD AND APPARATUS FOR BATCH FIXATING TISSUE SPECIMENS

[75] Inventors: John S. Sklenak, Sudbury; Robert F. Bowen, Burlington; Kenneth W. Dudley, Sudbury, all of Mass.

[73] Assignee: Raytheon Company, Lexington, Mass.

[21] Appl. No.: 536,848

[22] Filed: Jun. 12, 1990

[51] Int. Cl.⁵ .................... A61L 2/00; A01N 1/00; H05B 6/64
[52] U.S. Cl. ......................... 422/21; 422/36; 422/40; 435/1; 219/10.55 M; 219/10.55 R
[58] Field of Search ............... 422/21, 40, 36; 427/4, 427/45.1; 128/804; 219/10.55 A, 10.55 M, 10.55 D, 10.55 F, 10.55 R; 206/456; 312/209; 435/1

[56] References Cited

U.S. PATENT DOCUMENTS

| | | | |
|---|---|---|---|
| 3,601,249 | 8/1971 | Larsson | 206/456 |
| 4,330,696 | 5/1982 | Pomeroy et al. | 219/10.55 F |
| 4,681,996 | 7/1987 | Collins et al. | 219/10.55 M |
| 4,839,194 | 6/1989 | Malluche et al. | 427/4 |
| 4,891,239 | 1/1990 | Dudley et al. | 128/804 |
| 4,994,237 | 2/1991 | Login et al. | 422/21 |

OTHER PUBLICATIONS

Fisher Scientific, 1988, p. 1428.

*Primary Examiner*—Robert J. Warden
*Assistant Examiner*—Theresa A. Trembley
*Attorney, Agent, or Firm*—William R. Clark; Richard M. Sharkansky

[57] ABSTRACT

Method and apparatus for chemically fixating a plurality of tissue specimens in a multimode microwave oven. The tissue specimens are loaded in respective cassettes and then placed in radial alignment in a circular container that is filled with a fixation solution. Selective microwave shields such as metal disks with central apertures are located above and below the container which is then rotated on a turntable while being exposed to microwave energy in the microwave oven cavity. The shields are selected to provide a substantially uniform microwave field within the region occupied by the cassettes so that all of the tissue specimens are consistently and uniformly fixated.

13 Claims, 4 Drawing Sheets

METHOD AND APPARATUS FOR BATCH FIXATING TISSUE SPECIMENS

BACKGROUND OF THE INVENTION

This invention generally relates to the use of microwave energy to accelerate the rate at which a chemical preserving solution penetrates the walls of cells to provide tissue fixation, and more particularly relates to apparatus and method for batch fixating a plurality of tissue specimens.

As is well known, pathologists diagnose diseases by examining tissue specimens or samples from a biopsy or other similar medical procedure. Because it is important that the cells be examined in a state as close to the living state as possible, the tissue specimens are typically put through a chemical fixation process in order to stop the cells from degrading. More specifically, the specimens are typically emersed in a preserving solution which commonly includes formaldehyde. The preserving solution penetrates the walls of the cells and hardens the cell structure thereby preventing or greatly retarding subsequent cell degradation. A pathologist then subjects the specimens to various tests and examinations for diagnosis.

One significant problem of the above described fixation process is that it takes a relatively long period of time such as, for example, 4–8 hours for the preserving solution to penetrate cell walls. Accordingly, the fixation process may prevent a relatively fast diagnosis. Also, at least during the early stages of fixation, the cells may continue to degrade. The delay may cause the cells to change from their original living state and thus, in some cases, the proper diagnosis may be prevented or clouded.

Microwave energy has been used to speed up the rate at which the preserving solution penetrates cell walls during fixation. In the typical procedure, a tissue specimen or sample is placed in a vial containing a formaldehyde solution, and then the vial is exposed to microwave energy in a microwave oven. For reasons not fully understood but believed to be related to the vibration of molecules, the presence of the microwave field greatly increases the rate at which the fixation solution penetrates the cell walls. For example, the presence of a microwave field may reduce the typical fixation time period from several hours down to about one minute. This is important not only because it saves processing time, but also because the cells have less time to degrade and therefore the quality of the fixated tissue may be enhanced.

One microwave tissue fixating apparatus is described in U.S. Pat. No. 4,891,239 which is assigned to the same assignee as the present invention, and which is hereby incorporated by reference. Such apparatus has a single mode waveguide with a small aperture through which a vial containing a tissue specimen and the fixating solution is inserted. With such arrangement, the submerged specimen is exposed to a relatively uniform field of microwave energy, and the amount of microwave energy absorption in the specimen can be accurately controlled. Thus, favorable fixating results have been attained using this apparatus. However, one drawback of such apparatus is that it is not generally suitable for high volume production because only a single or just a few specimens can be simultaneously fixated. More specifically, there are limitations in the number and size of apertures that can be provided in a single mode waveguide and provide suitable impedance matching for vials inserted therein. Further, if a plurality of specimens were placed longitudinally along a waveguide, they would generally be exposed to different amounts of microwave energy thus resulting in non-uniform fixating results from specimen to specimen.

Conventional microwave ovens have been used to assist in tissue fixation. However, the distribution of microwave energy in a conventional microwave oven is not generally uniform enough so that a large plurality of tissue specimens can be simultaneously processed in batch operation with substantially identical and controlled results from specimen to specimen. Although rotating feed antennas and rotating turntables have generally improved the field uniformity in microwave ovens, the cavities of such microwave ovens still have so-called hot and cold spots. That is, the spacial distribution of energy is not uniform, and therefore the rate at which a lossy item absorbs microwave energy is a function of its spacial location within the microwave oven cavity. Also, there may be non-uniform exposure and hence absorption of microwave energy within a given specimen. Such non-uniform energy distribution is not suitable for batch processing tissue specimens because each specimen generally requires a relatively precise and controlled amount of exposure to microwave energy so as to fixate properly. If a vial in one spacial location receives the proper amount of exposure, another vial in another spacial location may receive too much or too little microwave exposure. If a specimen receives too much exposure, it will start to cook and important artifacts in the cells may be obscured or destroyed. On the other hand, if a specimen receives too little exposure, fixation may be incomplete and therefore not enough preserving solution will penetrate the cell walls to stop cell degradation.

SUMMARY OF THE INVENTION

An object of the invention is to provide an improved method and apparatus for fixating tissue specimens.

It is also an object to provide a method and apparatus for simultaneously fixating a large plurality of tissue specimens in a batch operation. Another object is to provide a method and apparatus for fixating many tissue specimens simultaneously in a multimode microwave oven cavity, and attain uniform and consistent fixating results in the tissue specimens.

In accordance with the invention, these and other objects and advantages are provided by an apparatus adapted for chemically fixating in a multimode microwave oven cavity, a plurality of tissue specimens in a batch operation, the apparatus comprising a tray having a circular bottom and outer wall wherein the tray is adapted for containing a fixation solution. A plurality of cassettes are submerged in the solution in the tray, and each cassette contains a respective one of the tissue specimens. Each of the cassettes has an elongated side that is radially aligned in the tray. The apparatus further includes means for rotating the tray within the microwave oven cavity, and means are provided for selectively shielding the tray from microwave energy in the cavity to provide a substantially uniform microwave field within the tray. As a result, there are substantially uniform fixating results of the tissue specimens after a predetermined time interval of activation of the microwave oven. Preferably, the uniformity of the microwave field is such that the maximum temperature differential between spacial locations in the solution is less than 15° F. after the solution has been heated more than 70° F. It is preferable that the selective shielding means comprises a metal disk supported on the outer wall. It is further preferable that the apparatus comprises a plurality of concentric rows of the radially aligned cassettes in the tray.

The invention can also be practiced by the method of simultaneously fixating a plurality of tissue specimens in a multimode microwave oven cavity, comprising the steps of providing a container, positioning the plurality of tissue specimens in the container wherein each of tissue specimens is positioned in a perforated cassette, filling the container with a fixating solution to immerse the tissue specimens, energizing the microwave oven for a predetermined time period which raises the temperature of the solution at least 60° F., and selectively shielding portions of the container during the energizing period to produce a maximum temperature differential of less than 15° F. within the solution.

With such arrangement, a batch or large plurality of tissue specimens emersed in a common fixation solution bath can be simultaneously exposed to microwave energy in a multimode microwave oven. Because the apparatus and method results in each tissue specimen receiving approximately the same microwave energy exposure, there is consistency of fixation from tissue specimen to tissue specimen. That is, each tissue specimen is properly fixated after a predetermined time interval of microwave exposure.

BRIEF DESCRIPTION OF THE DRAWINGS

The foregoing objects and advantages will be more fully understood by reading the Description of the Preferred Embodiments with reference to the drawings wherein.

DESCRIPTION OF THE PREFERRED EMBODIMENTS

Figure 1:
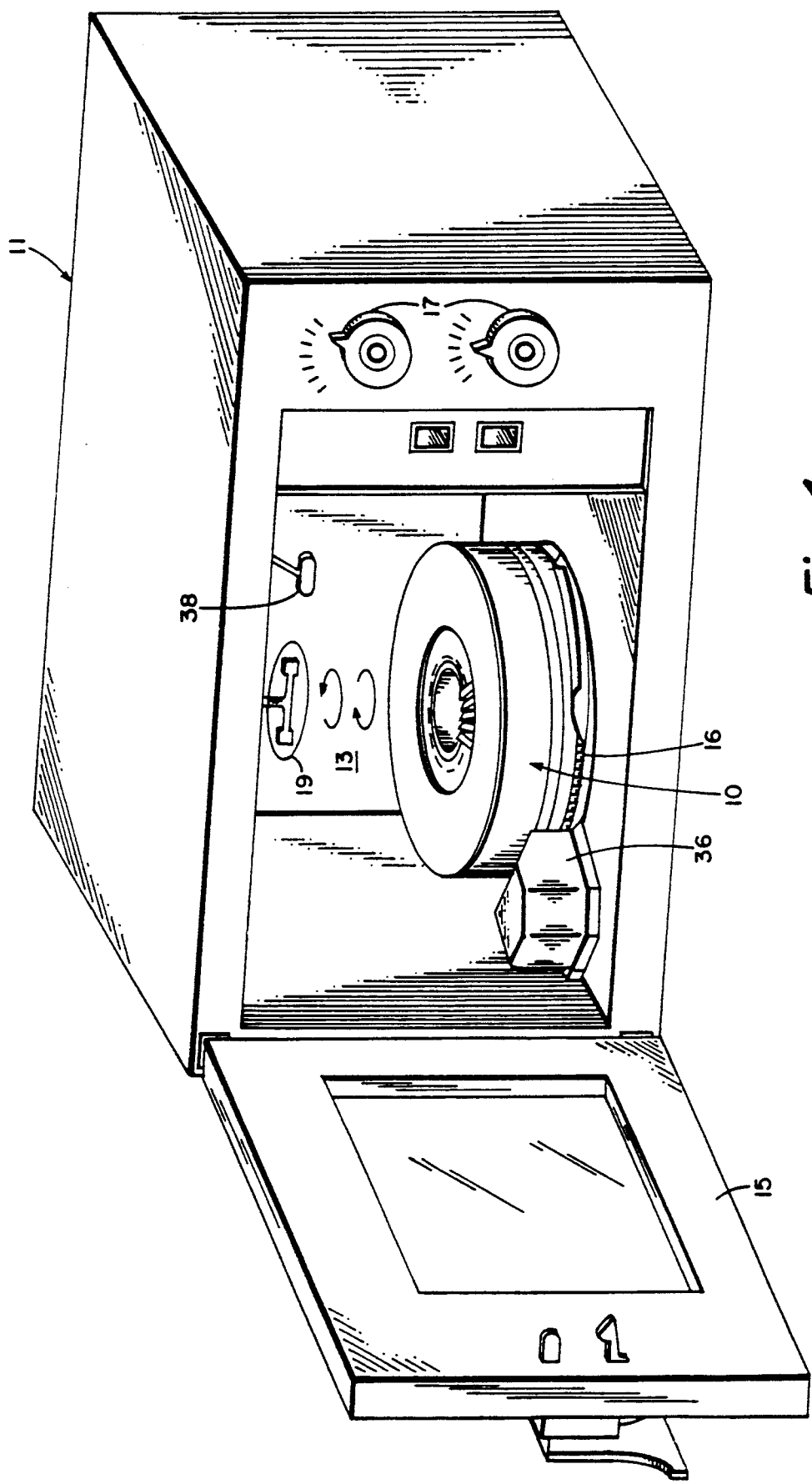
FIG. 1 is a front perspective view of a microwave oven containing a cassette tray for batch fixating a plurality of tissue samples or specimens.

Referring to FIG. 1, a cassette tray 10 is shown positioned on a turntable 16 in microwave oven 11. In accordance with well known practice, microwave oven 11 has a multimode cavity 13 sealable by door 15. Controls 17 are used to activate microwave oven 11, and microwave energy is directed downwardly in a relatively uniform pattern from a directive microwave feed antenna 19 which is rotated in one direction, here designated counterclockwise for convenience of discussion. Preferably, microwave oven 11 is a relatively high power oven such as, for example, a 1200 watt commercial oven identified as a Model No. RFS/8SE 1200 by Amana Refrigeration, Inc. of Amana, IA. Typically, microwave 11 operates at 2450 MHz.

Figure 2:
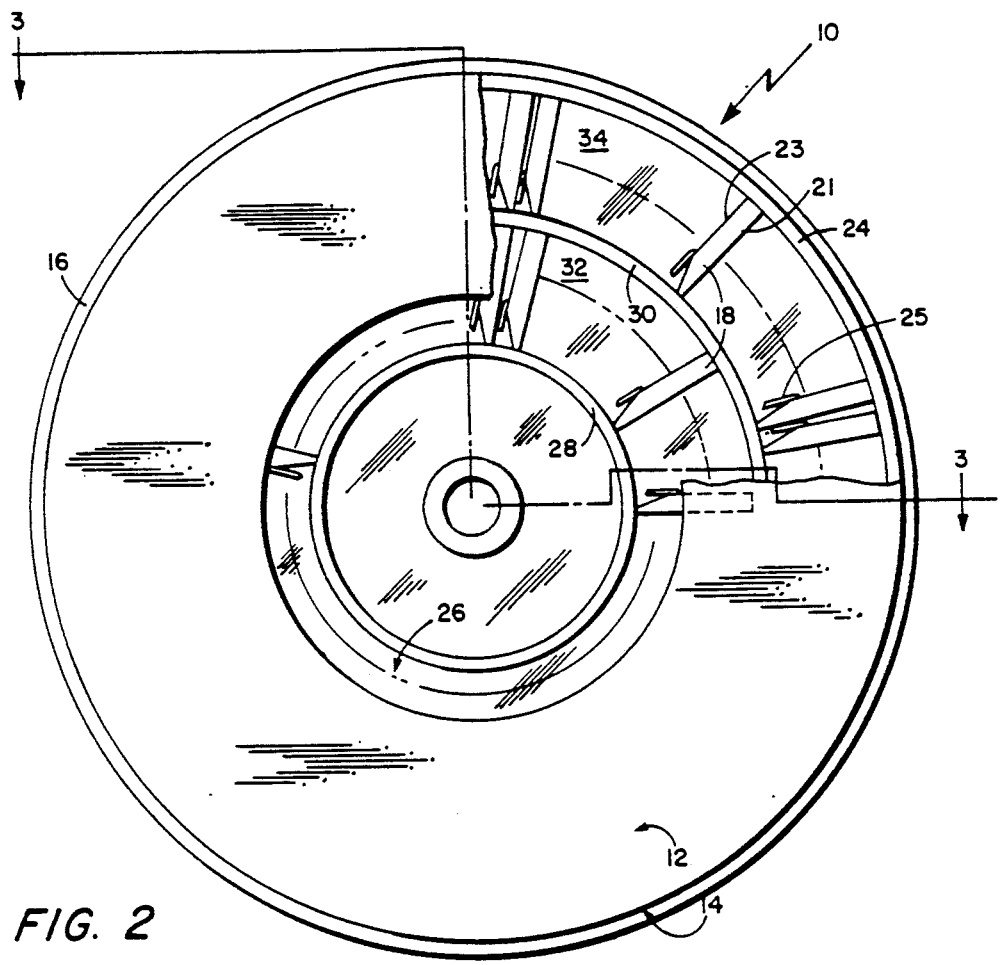
FIG. 2 is a partially broken away top view of the cassette tray containing a plurality of cassettes holding tissue specimens.
Figure 3:
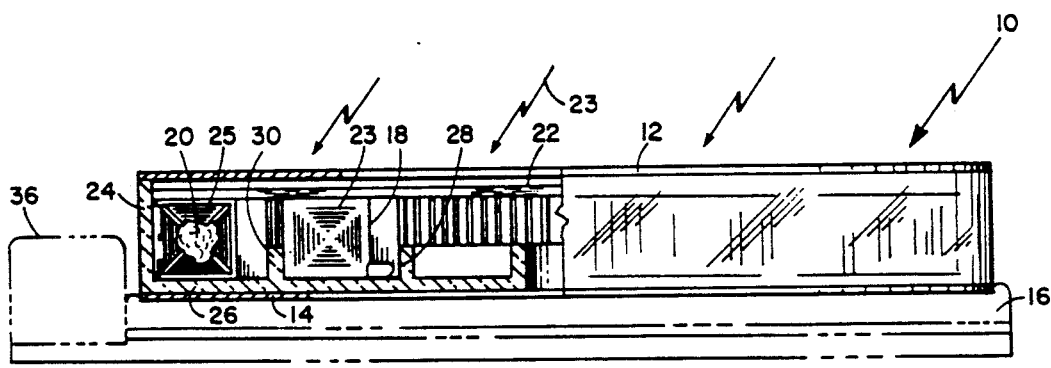
FIG. 3 is a view taken along line 3—3 of FIG. 2.

Referring to FIGS. 2 and 3, respective top and side views show cassette tray 10 or carousel to be a generally circular container having a circular bottom 26 or base, an outer peripheral wall or ring 24 integrally connected to the bottom 26, and one or more inner rings 28 and 30 protruding upwardly from the bottom 26 to a height less than outer ring 24. Thus, annular grooves 32 and 34 and formed in cassette tray 10. Preferably, cassette tray 10 is constructed from a high temperature plastic that is microwave transparent and can be fabricated to accurate dimensions and has non-hydrophilic stability. One such material is polysulfone manufactured by Amoco of Ridgefield, CT. In general, any member of the polysulfone polymer family or polymethylpentene would be suitable.

In preparing cassette tray 10 for fixation processing, a large plurality of cassettes 18 are prepared by loading a tissue specimen 20 or sample into each cassette 18. For example, one such cassette 18 may typically be identified by Catalog No. 15154-380 as distributed by Fisher Scientific of San Francisco, CA. Such cassettes 18 have a perforated base 21 and a perforated lid 23 so that the fixation solution 22 can pass to the specimen 20 stored therein. The lid 23 is connected to the base 21 by a living hinge, and after the tissue specimen 20 is positioned into the base 21, the lid 23 is closed and snap locked in place in conventional manner. Tab 25 is subsequently used to open lid 23 after the fixation process is completed. The dimensions of a typical cassette 18 are $1\frac{5}{8}'' \times 1\frac{1}{8}'' \times \frac{1}{4}$.

In one preferred embodiment for the particular above-identified cassette 18, cassette tray 10 has an outer diameter of approximately 10" with outer ring 24 having a height of $1\frac{3}{8}''$. Inner rings 30 and 28 have heights of 3/16" and are concentrically spaced at $1\frac{3}{4}''$ intervals. With such arrangement, approximately eighty-one cassettes 18 can be loaded edgewise with radial alignment in outer groove 34 as shown, and approximately forty cassettes can be loaded in inner groove 32. Although the preferred dimensions for cassette tray 10 are given, it is apparent that other sizes could be used to hold various numbers of cassettes. Also, in the embodiment shown, it is assumed that the cassettes 18 are relatively densely positioned in the grooves 32 and 34 of cassette tray 10, and therefore support each other in edgewise orientation. The bottom 26 of cassette tray 10 could be provided with vertical spacers (not shown) that would hold cassettes 18 in the same vertical orientation without relying on densely packed cassettes 18, but such spacers would typically reduce the cassette capacity.

Next, a fixation solution 22 is poured into cassette tray 10 to completely submerge all of the tissue specimens 20 stored in cassettes 18. The fixation solution 22 is free to flow over inner rings 28 and 30 because of their reduced heights, and also is free to flow through the perforated base 21 and lid 23 of each cassette 18 so that each specimen 20 is entirely emersed in fixation solution 22. Many different fixation solutions known in the art could be used; illustrative examples are as follows:

1. Karnovsky's fixative (2% formaldehyde, 2.5% glutaraldehyde and 0.025% calcium chloride in 0.1M sodium cacodylate buffer, pH 7.4).

2. Karnovsky's fixative (4% formaldehyde, 5% glutaraldehyde, and 0.05% calcium chloride in 0.03M sodium cacodylate buffer pH 7.2-7.4) and Malachite Green 1% (w/v) in 0.08M sodium cacodylate buffer pH 7.2-7.4.

3. 4% Glutaraldehyde and osmium tetroxide 0.5% (w/v), both dissolved in 0.08M sodium/cacodylate buffer pH 7.2-7.4.

4. 2.5% glutaraldehyde in 0.1M sodium cacodylate, pH 7.4 with 0.25 mM $CaCl_2$ and 0.5 mM $MgCl_2$ (primary fixative).

More details of these solutions are explained in "Microwave Cookbook of Pathology—The Art of Microscopic Visualization"; Second Revised Edition; by Mathildie E. Boon and L. P. Kok; Coulomb Press; 1988; pp. 184-189, which is hereby incorporated by reference. The solution is poured into the cassette tray 10 to totally submerge the cassettes 18 and the tissue specimen 20; for example, the solution 22 may have a depth of 1.25 inches.

Next, bottom apertured disk 14 or washer is placed below bottom 26, and top apertured disk 12 or washer is seated and supported on outer ring 24 or wall. Top disk 12 preferably has an outer diameter of 10" which is the same as outer wall 24, and has an inner diameter of 4.5". Bottom disk 14 preferably has an outer diameter of 10" and an inner diameter of 5". Both metal disks 12 and 14 are constructed from an electrically conductive material such as a metal having a thickness of approximately 0.30". Metal disks 12 and 14 are used to provide selective microwave energy shielding of cassette tray 10, and thereby contribute to attaining a substantially uniform distribution of microwave energy within the cassette containing volume of cassette tray 10.

Cassette tray 10 containing the specimen loaded cassettes 18 is then positioned on turntable 16. In the preferred arrangement, turntable 16 may be integrated into the microwave oven 11. For example, the turntable 16 may have a microwave transparent supporting surface and be built into the floor of the microwave oven cavity 13. Here, turntable 16 is shown to be a unit that is removably supported on the floor of the microwave oven. An example of such a turntable 16 is Model 509-11 manufactured by Anchor Hocking Corp. of Lancaster, OH, and modified to operate with a 9 volt rechargeable battery. With such configuration, turntable 16 would typically remain positioned within the microwave oven cavity 13, and the loaded cassette tray 10 would be set onto the turntable 16 in that position. The motor 36 of the turntable 16 is then activated so that the turntable 16 rotates in the opposite direction, here designated clockwise, from the microwave feed antenna 19. It is preferable that the turntable 16 have a relatively fast angular velocity such as, for example, 25 seconds/revolution or faster.

With the above described configuration of cassette tray 10, the arrangement of cassettes 18, the turntable 16 and microwave oven 11, each of the tissue specimens 20 is subjected to approximately the same amount of microwave energy, and thus there is fixation consistency from specimen to specimen so that a large plurality of specimens 20 can be fixated simultaneously in a batch. Accordingly, the labor involved in processing a large plurality of specimens 20 is reduced, and many more specimens can be processed in a given time period than was possible heretofore. The duration of microwave energy exposure would, of course, be a function of the power of the microwave oven, the size of cassette tray 10, the number of specimens 20 being processed, and the volume of the fixation solution 22. To obtain consistent fixation results from fixation process to fixation process, it is preferable that the same measure of fixation solution 22 always be used and that the cassette tray 10 always be completely loaded with cassettes 18 whether or not that many specimens are available for processing; it may be desirable to position dummy loads in cassettes 18 not containing tissue specimens 20. One method of determining the appropriate and proper activation time of the microwave oven 11 is to run a number of trials and have a pathologist check the specimens 20 after each run for proper fixation. The temperature of the fixation solution 22 can be used as a measure of the amount of microwave energy actually absorbed by the specimens 20. For example, it may be determined that with a particular cassette tray 10 and load of cassettes 18, the specimens 20 are properly fixated when the fixation solution 22 reaches a particular predetermined temperature such as, for example, 150° F. Then, during future runs, the temperature of the fixation solution 22 can be monitored by an appropriate thermal sensor such as an infrared sensor 38 as shown in FIG. 1, and the microwave oven 11 can be shut off or deactivated when the solution 22 reaches that temperature.

A number of factors contribute to the above described arrangement enabling relatively consistent fixation results from fixation procedure to fixation procedure, and also from specimen to specimen within a fixation procedure or run. The feed antenna 19 of the microwave oven 11 has a directive pattern, and by rotating the antenna 19, the pattern is rotated so as to spacially move the "hot" and "cold" spots to time average the field to provide enhanced uniformity. The cassette tray 10 is rotated through the moving field to further randomize and thus further average the microwave energy to which a given specimen 20 is subjected on a time-averaged basis. Further, the turntable 16 and cassette tray 10 may be placed off center from the antenna 19 so that effective rings of differing field intensity are not permitted to be set up. The cassette tray 10 is round and, therefore, there are no two-dimensional outward protrusions such as corners that would be subjected to increased exposure to the microwave energy field. The radial arrangement of the cassettes 18 provides radial symmetry which results in a relatively uniform mass such that microwave energy enters radially in a uniform manner around the circumference of cassette tray 10. Without using aperture disks 12 and 14 to selectively shield cassette tray 10, cassettes 18 in the outer groove 34 would receive significant radiation of microwave energy entering from both the top and the side, while cassettes 18 in the inner groove 32 would receive significant radiation only from the top; microwave energy entering from the side would be substantially absorbed in the outer groove 34 before reaching the inner groove 32. Accordingly, the shielding is used to provide substantially the same microwave energy exposure to a specimen 20 regardless of its loading position within cassette tray 10. It is also noted that there are high microwave field intensities at the edges of disks 12 and 14. Therefore, it is preferable that the respective outer peripheries extend beyond the cassettes 18 in groove 34 as shown, and that the respective inner peripheries extend inwardly to approximately the mid portion of the cassettes 18 in groove 32.

It is generally held that the increase in fixation rate caused by performing fixation in a microwave energy field is due to the effect of the E-field on the cells rather than the microwave thermal effect on the fixation solution 22 or tissue specimens 20. Further, microwave assisted fixation of a given tissue specimen 20 generally requires a precise and controlled amount of microwave exposure so that complete fixation occurs and the tissue specimen 20 is not overheated. Accordingly, batch-mode or simultaneous processing of a large plurality of similar tissue specimens 20 generally requires relatively steady state or time averaged E-field uniformity over the volume in which the tissue specimens 20 are located so that all specimens 20 are similarly or consistently processed. Unfortunately, E-field distribution within a multi-mode microwave oven cavity 13 is not easily measured nor calculated, and the E-field within an operating structure such as cassette tray 10 is even more complex. Thus, although the E-field uniformity is the phenomenon of importance in evaluating the suitability of a microwave batch fixation apparatus, a more conveniently measured parameter is desirable to study more easily the performance of a cassette tray 10. The distribution or profile of temperature rise within a lossy material is generally indicative of the uniformity of the microwave field in that material, and therefore a procedure using measured temperatures was developed in order to study the effects of various parameters and apparatus geometries on E-field uniformity. In particular, tests were run with various operating configurations so that the effect of various operating parameters on the E-field uniformity could be analyzed. Using such approach, existing batch process fixation apparatus can be evaluated, and also new apparatus can be developed which optimize for other operating configurations such as, for example, with a different microwave oven 11 having a different microwave energy pattern.

Figure 4:
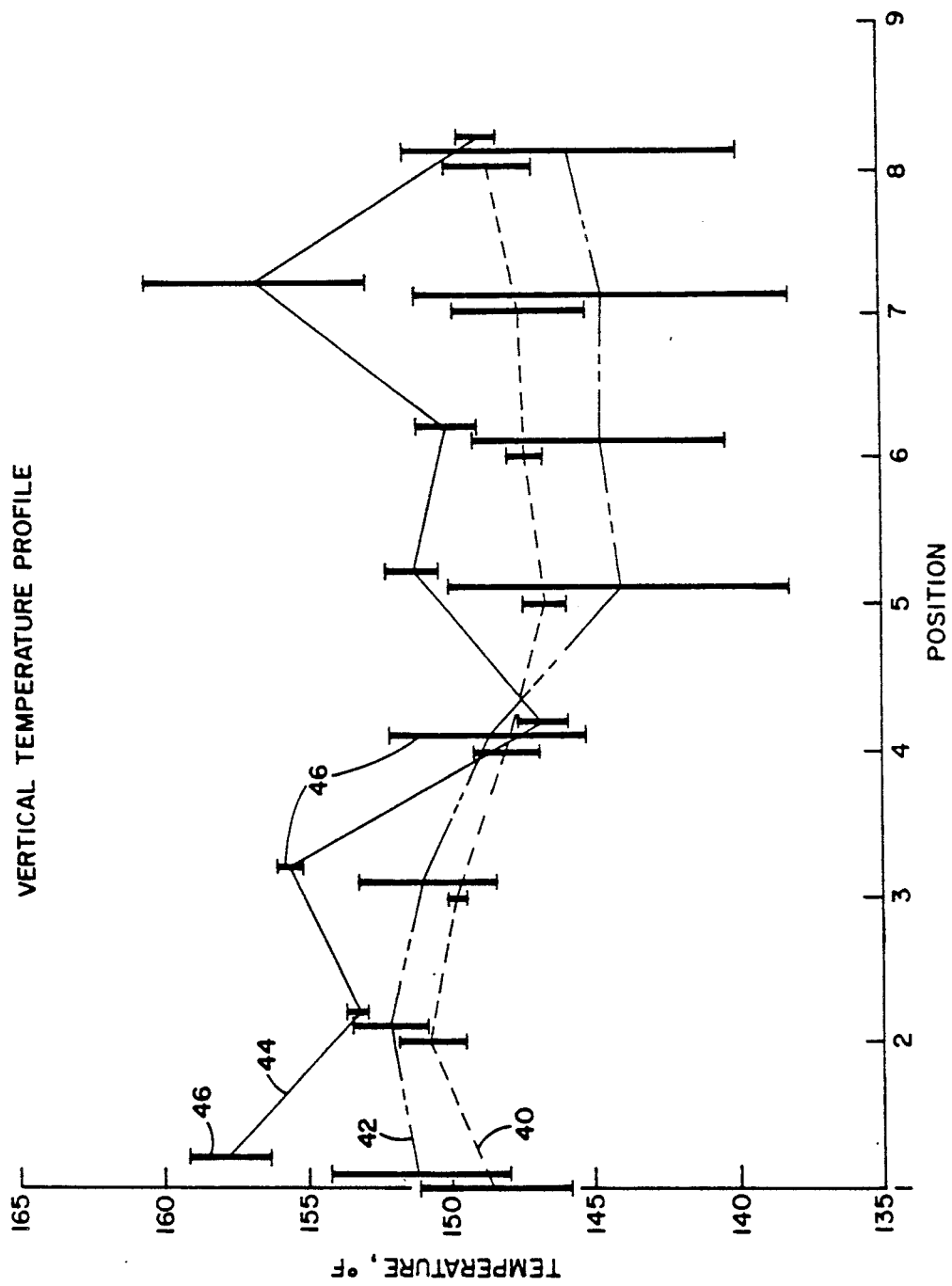
FIG. 4 is a graph showing temperature data at specified positions and specified depths within the cassette tray after processing with various operating conditions.
Figure 5:
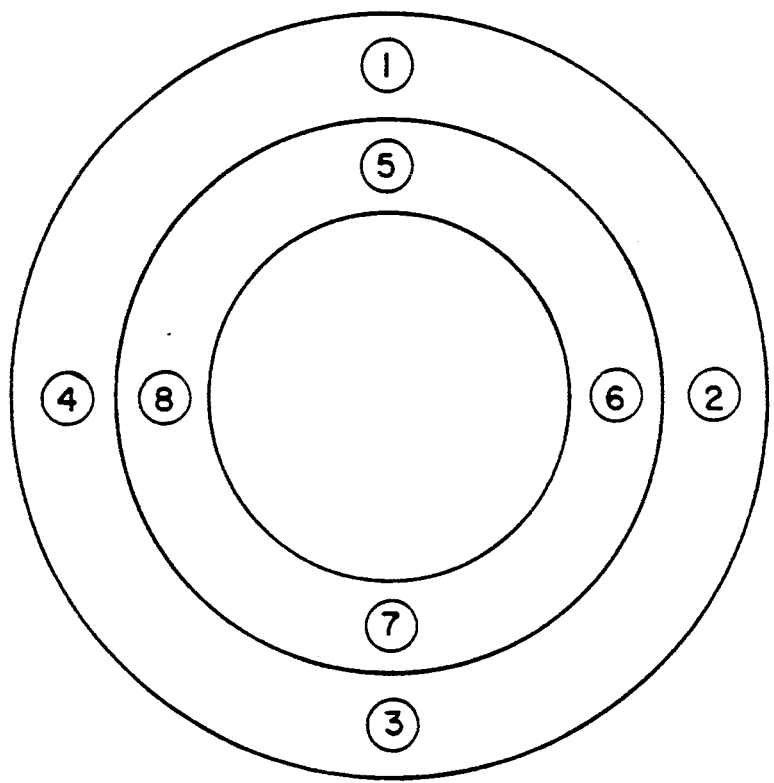
FIG. 5 is a diagram showing the positions in the cassette tray where the temperature data in FIG. 4 was taken.

FIG. 4 displays test data on the above described evaluation and study method. In particular, tissue specimens 20 were loaded into respective cassettes 18 and the cassettes 18 were positioned into respective grooves 32 and 34 until cassette tray 10 was completely full as described above. An isotonic saline liquid (0.9% weight/volume sodium chloride solution) having an initial temperature of approximately 72° F. was then poured into cassette tray 10 to a depth of approximately 1.25 inches so that cassettes 18 were completely submerged. The cassette tray 10 was then positioned in an Amana Model RFS/8SE microwave oven which was activated for 6 minutes. The temperature within the saline liquid was then immediately measured at predetermined positions as identified in FIG. 5 with the front of the microwave oven 11 at the bottom of the view. Specifically, a Luxtron Model 750 Fluoroptic Thermometry System and Luxtron Model MSA-02 Temperature Measuring Probes were used. At each position as indicated in FIG. 5, probes were located at three different depths within the saline liquid. In particular, probes were used to measure the temperature at 0.27", 0.52", and 0.77" from the bottom 26 of the cassette tray 10. Accordingly, three vertically aligned temperatures were measured at eight different positions resulting in 24 spacial location temperature measurements. The temperature readings were taken as quickly as possible to minimize temperature normalization with the saline liquid, and the positions were read in the following sequence: 1-7-2-8-5-3-6-4. The same procedure was then followed for other 6-minute trial runs to be described.

Referring to FIG. 4, the temperature readings were plotted for each of the positions as indicated in FIG. 5. Each data point includes a vertical bar 46 corresponding to the range of the upper and lower temperatures of the three temperature readings taken at the above identified vertical heights at each position. For example, if a vertical bar 46 is short, it indicates that the three readings at the particular position were relatively close indicating vertical uniformity of the E-field at that particular position. Conversely, if a vertical bar 46 is relatively tall, it indicates that the upper and lower of the three temperature readings are relatively far apart indicating a relatively large temperature differential $\Delta T$ in the vertical direction at that position.

Lines 40, 42, and 44 each connect the midpoints of vertical bars corresponding to data taken on three sequential 6 minute microwave oven trial runs. The vertical bars connected by line 40 represent temperature data taken when metal disks 12 and 14 were used as described above, and the cassette tray 10 was rotated at 25 seconds/revolution on turntable 16. With such arrangement, the temperature and thus the E-field is relatively uniform throughout the cassette tray 10. The vertical disparity of line 40 gives a general indication of the planar uniformity, and the heights of the various bars 46 of line 40 gives an indication of the vertical uniformity and thus the E-field uniformity at the particular positions. The highest temperature reading was approximately 151.7° F. at the middle level of position 2, and the lowest temperature reading was approximately 145° F. at the top level of position 5. Therefore, the maximum measured temperature differential $\Delta T$ within cassette tray 10 was approximately 6.7° F.

The vertical bars 46 connected by line 42 represent temperature data taken when metal disks 12 and 14 were not used, and cassette tray 10 was rotated at 25 seconds/revolution on turntable 16. As can be seen, the vertical disparity of line 42 is much greater than line 40. The highest temperature reading was approximately 154.2° F., at the middle level of position 1, and the lowest temperature reading was approximately 138.4° F. at the bottom level of position 5. Therefore, the maximum measured temperature differential $\Delta T$ within cassette tray 10 without using metal disks 12 and 14 for shielding was 15.8° F.

The vertical bars 46 connected by line 44 represent temperature data taken with metal disks 12 and 14 being used, but without any rotation by turntable 16. As indicated by line 44, there is relatively large disparity in the temperature profile within cassette tray 10 in this operational configuration without the use of turntable 16. The highest temperature reading was approximately 160.5° F. at the top level of position 7, and the lowest temperature reading was approximately 146° F. at the top position of position 4. Therefore, the maximum temperature differential $\Delta T$ within cassette tray 10 without using turntable 16 was approximately 14.5° F.

As can be seen from FIG. 4, the lowest temperature differential $\Delta T$ within cassette tray 10 is accomplished by using metal disks 12 and 14 and rotating the cassette tray 10 on turntable 16. By comparing the data of the three different operational trial runs as indicated by lines 40, 42, and 44 as described above, the effect of various configurations and operational parameters can be determined. It is also apparent that other operational parameters could also be studied in a similar manner. Such information and such procedure can be used to optimize a cassette tray 10 for a particular operating configuration so as to improve the E-field uniformity and thus the quality of specimens 20 fixated in batch processing.

A number of fixation runs were made using the general procedure described with respect to FIG. 4. After such runs, tissue specimens 20 were placed under a microscope and observed. It was found that proper fixation occurred when the fixation solution 22 had risen approximately 70°-80° F. from an initial temperature of approximately 72° F. and, for the operating conditions described herein, that took approximately six minutes. It appears that when the temperature differential ΔT between the hottest and coldest spacial locations within cassette tray 10 for these conditions is greater than 15° F., the E-field is not uniform enough to have consistent and acceptable results throughout the entire batch. That is, if some specimens 20 are properly fixated, there will be others that will be underexposed or overexposed in the microwave E-field such that they will not be properly fixated or their artifacts may be obscured or destroyed. Somewhat consistent fixation results throughout the cassette tray 10 occur when ΔT is 15° F. or less, and preferably ΔT is 8° F. or less.

This concludes the description of the preferred embodiment. However, a reading of it by those skilled in the art will bring to mind many alterations and modifications without departing from the spirit and scope of the invention. Accordingly, it is intended that the invention be limited only by the appended claims.

What is claimed is:

1. Apparatus adapted for chemically fixating in a multimode microwave oven cavity a plurality of tissue specimens in a batch operation, said apparatus comprising:

a tray having a circular bottom and an outer wall, said tray containing a fixating solution;

a plurality of cassettes submerged in said solution in said tray, each of said cassettes containing a respective tissue specimen, each of said cassettes having an elongated side radially aligned in said tray;

means for rotating said tray within said microwave oven cavity; and means for selectively shielding said tray from microwave energy in said cavity to provide a substantially uniform microwave field within said tray thereby providing substantially uniform fixating results of said specimens after a predetermined interval of activation of said microwave oven.

2. The apparatus recited in claim 1 wherein said interval of microwave activation heats said solution more than 70° F., and the maximum temperature differential within said solution in said tray is less than 15° F.

3. The apparatus recited in claim 1 wherein said selective shielding means comprises a metal disk supported on said outer wall, said disk having a central aperture.

4. The apparatus recited in claim 3 comprising a plurality of concentric rows of said radially aligned cassettes in said tray.

5. The apparatus recited in claim 4 wherein said selective shielding means further comprises a metal disk positioned under said tray and having a central aperture.

6. The method of fixating a plurality of tissue specimens in a batch operation within a multimode microwave oven cavity, comprising the steps of:

providing a circular container having a bottom and an outer wall;

positioning a plurality of tissue specimen cassettes in said container wherein each cassette has an elongated side radially aligned with said tray, each of said cassettes containing a respective one of said tissue specimens;

filling said container with a fixating solution to immerse said tissue specimens;

positioning a selective shield on said container, said shield comprising a metal disk having an aperture in the center;

positioning said container with said solution and cassettes in said microwave oven cavity; and rotating said container while energizing said microwave oven cavity for a predetermined time period wherein the temperature of said solution is raised by at least 60° F. and the maximum temperature differential within said solution is less than 15° F.

7. The method recited in claim 6 further comprising the step of monitoring the temperature of said solution and deactivating said microwave energization when a predetermined temperature is reached.

8. Apparatus adapted for chemically fixating in a multimode microwave oven cavity a plurality of tissue specimens in a batch, said apparatus comprising:

a plurality of cassettes each containing a respective tissue specimen, said cassettes each having an elongated side;

a tray holding said cassettes, said tray having a circular bottom, an outer wall, and at least two concentric annular grooves;

said cassettes being arranged in annular rows within said respective grooves wherein the elongated side of each cassette is radially aligned with said circular bottom of said tray;

a fixating solution in said tray immersing said cassettes;

means for rotating said tray within said microwave oven cavity; and means for providing a substantially uniform microwave field within said grooves of said tray wherein each of said tissue specimens is exposed to substantially the same time averaged exposure to microwave energy, said providing means comprising a metal disk having a central aperture positioned on said tray to provide selective shielding of microwave energy.

9. The method of simultaneously fixating a plurality of tissue specimens in a multimode microwave oven cavity, comprising the steps of:

providing a circular container;

positioning a plurality of tissue specimens into respective ones of a plurality of perforated cassettes each having an elongated side;

placing said cassettes in said circular container with the elongated sides being radially aligned therein;

filling said container with a fixating solution to immerse said tissue specimens;

positioning said container in said microwave oven cavity;

energizing said microwave oven for a predetermined time period to raise the temperature of said solution at least 60° F.; and selectively shielding portions of said container during said energization period to provide a maximum temperature differential in said solution of less than 15° F.

10. The method recited in claim 9 wherein the maximum temperature differential in said solution is 8° F. or less.

11. The method recited in claim 9 further comprising the step of rotating said container while energizing said microwave oven.

12. The method recited in claim 11 further comprising the step of rotating a microwave feed antenna of said oven in a rotation direction opposite the rotation of said container.

13. The method recited in claim 9 wherein said shielding is provided by a metal disk positioned on said container.

* * * * *